United States Patent [19]

Mercer

[11] Patent Number: 4,845,730
[45] Date of Patent: Jul. 4, 1989

[54] SELECTIVE ON-LINE MEASUREMENT OF FILLER COMPONENTS IN PAPER

[75] Inventor: Peter G. Mercer, Burgbrohl, Fed. Rep. of Germany

[73] Assignee: Paul Lippke GmbH Und Co. KG, Neuwied, Fed. Rep. of Germany

[21] Appl. No.: 134,716

[22] Filed: Dec. 18, 1987

[30] Foreign Application Priority Data

Dec. 20, 1986 [DE] Fed. Rep. of Germany ....... 3643764

[51] Int. Cl.$^4$ .................... G01N 22/223; G01N 33/34
[52] U.S. Cl. ......................................... 378/53; 378/51
[58] Field of Search ...................... 378/51, 53, 54, 64, 378/68, 69; 250/339

[56] References Cited

U.S. PATENT DOCUMENTS 3,904,876  9/1975  Arendt .................................. 378/53
4,696,023  9/1987  Kuusi .................................... 378/53

FOREIGN PATENT DOCUMENTS

2910673  9/1980  Fed. Rep. of Germany .
0046146  3/1982  Japan ..................................... 378/51
8301113  3/1983  PCT Int'l Appl. .................. 378/83

Primary Examiner—Carolyn E. Fields
Assistant Examiner—Joseph A. Hynds
Attorney, Agent, or Firm—Quarles & Brady

[57] ABSTRACT

By applying infra-red radiation as well as beta-radiation measurement techniques combined with a characteristic x-radiation measurement technique using a mono-energetic and stable x-ray source, it is possible to carry out a very accurate selective filler measurement on a moving paper web containing two fillers, provided that at least one of the two fillers has a distinct absorption band in the infra-red radiation range. The web is irradiated by the individual measurement rays, and the detected measurement signals resulting from the irradiations of the web are processed in a micro-computer.

8 Claims, 4 Drawing Sheets

SELECTIVE ON-LINE MEASUREMENT OF FILLER COMPONENTS IN PAPER

FIELD OF THE INVENTION

The field of the invention is selective on-line measurement of filler components in paper or similar materials, and particularly, the selective measurement of fillers in moving paper webs consisting of a stock-mix made up of a base material and two filler components, and, possibly, containing a further substance such as water.

BACKGROUND OF THE INVENTION

It is known that by applying beta-rays the basis weight or grammage of a moving paper web can be measured. Furthermore, it is known that by simultaneously applying beta-radiation and a characteristic x-radiation to the moving paper webs the total ash and filler content can be measured, albeit on the condition that either there is only one single filler in the paper web, namely kaolin (clay), talcum or a filler component containing pure $CaCO_3$. In the case of filler component mixtures containing kaolin, talcum, $CaCO_3$ and/or $TiO_2$, the total ash content measurements require the filler component recipe, i.e. the relation between the individual filler components.

In the above conventional measurement technique a natural radioactive Fe-55 radiation source is used as source for the characteristic x-radiation. The Fe-55 radiation source emits a quantum radiation with a mono-chromatic energy of 5.9 keV. The known filler-measurement technique makes use of the fact that, by using the mono-energetic measurement ray from the Fe-55 radiation source, a strictly exponential absorption law with clearly-defined absorption coefficients applies. This means that all the radiation extinction contributions of the various components of the paper web tested add up mathematically to a resulting extinction signal.

Furthermore, a measurement method using fluorescence x-ray analysis to measure the filler content in paper webs is known. With this method, a filler component mix containing Mg, Ca, Al and Ti can be measured. Use is made in this regard of the fact that each of the elements Mg, Ca, Al and Ti has a specific fluorescence wavelength. The content of each of these elements in the paper web tested is determined by measuring the specific fluorescence of each element per unit of time. This analytical method is the standard method applied nowadays in instruments for the laboratory analysis of samples but, to date, it has not caught on for on-line application because of serious apparatus-related problems. The problems are basically: the temperature sensitivity of the scintillation meter for the detection of the fluorescence radiation; measurement of radiation in scatter mode with its attendant problems of errors caused by changes in the position of the web in the measuring gap.

On the other hand, it is known from the German Pat. No. 2,910,673 that the absolute content or the basis weight of a substance in a moving web can be measured with a high degree of accuracy by applying infra-red rays and beta-rays, as long as both the substance to be measured and a further substance which forms a major component of the web each have a distinct absorption band in the infra-red radiation range and the substances in the material of the web are mixed, i.e. form a stock mix. This well-known measuring method is used especially to determine the absolute water content in paper webs which have cellulose as their main substance. The measurement in the infra-red radiation range is done with the help of a measurement wavelength which is absorbed by the water, a measurement wavelength absorbed by the cellulose and a reference wavelength which is not appreciably absorbed by either the water or the cellulose. By comparing the radiation intensity measured with the measurement wavelength for the water with the radiation intensity of the reference wavelength, an extinction signal is obtained which represents a measure of the absolute water content in the paper web. This measurement signal for the absolute water content is, however, distorted by a lengthening of the infra-red measuring ray path caused by the opacity (internal scatter) of the paper. Therefore, to determine the true absolute content of the water in the paper web, the measurement result obtained is multiplied by a correction value which takes account of the structural characteristics of the mixture of water and cellulose in the web. This correction value is determined by comparing the measurement result for the entire basis weight of the paper web obtained using beta-rays with the measurement signal for the basis weight of cellulose obtained using infra-red rays. The determination of this correction factor is based on the assumption that the distortion of the measurement signal for the basis weight of the water, which is obtained from infra-red measurement, is proportional to that of the measurement signal for the cellulose obtained using infra-red measurement and that the measurement result for the total basis weight of the web, obtained using beta-rays, corresponds to the true basis weight of the cellulose because of the low percentage share of water in the total basis weight. Also of importance in this connection is the fact that the measurement by means of beta-rays is not, of course, influenced by the structural characteristics of the web.

In the known state of the art according to German Pat. No. 2,910,673, two reference wavelengths are generally used in the infra-red radiation measurement technique to eliminate wavelength-dependent losses of infra-red rays. With the help of both the reference wavelengths, it is possible to determine a corrected reference value for the measurement signal obtained with each measurement wavelength.

The four-wavelengths measurement method according to German Pat. No. 2,910,673 is not only intended for use in measuring the water content in paper but in general for measurements on paper webs in which the content of a substance in the material of the web is to be measured, provided that the substance to be measured is mixed with the other substances in the web and that, like the substance to be measured, a further substance which can give rise to a false or distorted measured value has also got a distinct absorption band for infra-red radiation. Thus the known measurement method could also be used to measure the content of a filler component in a web, as long as the filler component has a distinct absorption band in the infra-red radiation range. However, the problem arises that in the case of filler components present in the paper web, the approximation that the total basis weight of the web measured with beta-rays corresponds to the true basis weight of the cellulose no longer applies. Furthermore, when, in addition to a first filler component, a second filler component is selected to be present in the material mix, one of the two filler components does not generally have a distinct absorption band in the infra-red radiation range. The measurement method according to German Pat. No. 2,910,673 is thus not suitable for the selective filler measurement of moving webs containing two filler components.

In the paper industry there is a general pressing need for measuring equipment which can determine the distribution of two filler components, e.g. kaolin (clay) and calcium carbonate, in moving webs of filled or coated paper. This need exists especially when waste paper is added in an unregulated way to the paper pulp used to produce the paper web, or when broke of pigment-coated paper is recycled into the raw paper pulp and an exact knowledge of the filler composition gets lost in the process.

On the other hand, the fillers used for the manufacture of paper generally contain compounds of metals such as aluminum in kaolin and satin-white, calcium in calcium-carbonate and satin-white, titanium in titanium dioxide and barium in barium sulphate. Such metals have, of course, characteristic absorption characteristics in a radiation energy range of several keV which are conducive to the highly selective measurement of the relevant individual fillers, essentially independent of the filler composition—that is in the presence of the base material cellulose and also moisture contained in the web.

These characteristics of the fillers form the basis for the measurement method using the x-ray fluorescence analysis which has already been mentioned above.

In principle, the problem of selective filler measurement could also be solved for example by taking two separate measurements for two different fillers present in the stock-mix and then by solving a system consisting of two linear equations with two unknown quantities which represent the content of each of the two fillers respectively. The ability to adjust the energy of an x-ray which emits a continuous radiation appears to offer a solution to the problem in question. Two sets of filler-measuring equipment with suitably adjusted energy spectra could be used. The one set of measuring equipment could be adjusted to the energy range at the resonant point of the one filler component and the other to the energy range at the resonant point of the other filler component. In the resonance range, namely, the relative absorption coefficients differ most from each other, so that, as far as selectivity is concerned, one would obtain optimal conditions.

The emission spectrum of an x-ray source emitting continuous radiation is, however, extremely broad. The half-band-width of the spectrum amounts to about one third of the maximum energy. Due to the broad spectrum of the continuous radiation the absorption coefficient of the substance to be measured changes with increasing weight as a higher proportion of the low energy radiation is absorbed. This means that the absorption law as a function of a higher order would have to be empirically determined. The absorption law of filler measuring equipment which uses continuous radiation would, therefore, be dependent on the system. The advantage of the adaptability of the radiation energy in the case of filler measuring equipment which uses continuous radiation would, therefore, be completely cancelled out if the equation system contained non-linear terms. Furthermore, there is the problem of instability of the measurement as a result of drift in the high-voltage supply of the x-ray tubes.

SUMMARY OF THE INVENTION

The present invention relates to a method and system for selectively measuring fillers in moving webs, and particularly, for determining the content of the two filler components in a stock-mix of a moving paper web. The invention includes the simultaneous or combined application of infra-red rays, beta-rays and a characteristic x-radiation to the moving paper web and the processing of measurement signals resulting from said application.

A general object of the invention is the selective measurement of two filler components in a moving paper web with a high degree of accuracy and in a simple and practicable manner. This is achieved by the invention, provided that at least one of the two filler components, e.g. the first filler component, has a distinct absorption band in the infra-red radiation range. This is the case for kaolin (clay) and talcum. Therefore, by means of infra-red radiation it is possible to obtain a measurement signal for the absolute content or the basis weight (grammage) of the first filler component which is essentially independent of the other substances in the paper web. However, this measurement signal is distorted because of the internal scatter which occurs in the web. To determine a correction factor which takes the distortion of the infra-red measurement signal into account, the invention is based on the simultaneous application of infra-red rays, beta-rays and a characteristic x-radiation to the web to be measured. The evaluation of the measurement signals obtained with these rays is based on the realization that a correction factor which takes the actual internal scatter or opacity of the web into account can be obtained by forming the ratio between the measurement signal obtained using beta-rays (representing the total basis weight of the web) and a "sum-signal", the latter being obtained by adding up the measurement signals for the basis weights of all the substances present in the web obtained by means of infra-red radiation. The difficulty which arises in this regard, viz. that such a measurement signal cannot be obtained for the second filler component because it lacks a distinct absorption band in the infra-red radiation range, is overcome by replacing the signal that cannot be measured by a fictitious or theoretical "measurement" signal which is generated by further assuming that this theoretical signal, if it could be measured by applying infra-red radiation, is distorted, i.e. affected by the opacity of the web, in the same proportion as the measurement signal for the basis weight of the first filler component actually measured by means of infra-red radiation.

The assumptions described above then permit the determination of the correction factor using the measurement signals obtained with the three types of radiation. This correction factor can be applied not only to the measurement signal for the basis weight of the first filler component obtained using infra-red radiation but also to each of the infra-red radiation measurement signals for the basis weight of a substance present in the web which has a distinct absorption band in the infra-red radiation range.

In the present invention, the method and equipment described in German Pat. No. 2,910,673 can essentially be used to apply the infra-red radiation and to obtain the measurement signals for the basis weights of the substances in the web which can be measured with infra-red radiation. Preferably two reference wavelengths are used in addition to the various specific measurement wavelengths. By using two reference wavelengths a more accurate reference value for the radiation intensity signals measured at the specific measurement wavelengths can be determined, furthermore, if necessary, the radiation intensity of a substance measured at the infra-red radiation measurement wavelength absorbed by this substance can be corrected in respect of a distortion of intensity which is caused in the measurement wavelength of this substance by a substance which is related to a different specific wavelength.

The measurement of the total basis weight of a moving web with beta-radiation is a well-known measurement technique and one with which a man versed in this specific field of the art is familiar. Unlike infra-red radiation, beta-radiation, being a corpuscular radiation, is not influenced by the structural characteristics of the web to be measured. Thus, beta-radiation generally provides a measurement signal for the total basis weight (total grammage) of the web. For the measurement of a paper web this means that the contribution of the cellulose, the contribution of both the filler components and the contribution of the water are combined in the measurement signal obtained by means of beta-radiation. The characteristic x-radiation is preferably implemented by the quantum radiation of the natural radioactive radiation source Fe-55, which radiation occurs at 5.9 keV. A man versed in this specific field of the art is familiar with the Fe-55 radiation source and has the necessary radiation detectors at his disposal.

Unlike the continuous x-ray radiation (bremsstrahlung) which covers a broad spectral range, the characteristic x-radiation consists of individual characteristic lines. Although the characteristic x-radiation, or more precisely the quantum radiation emitted by the Fe-55 radiation source, cannot be adjusted to a specific energy and thus appears to be less suitable for achieving the object of the invention than the adjustable continuous x-ray radiation, it is precisely this mono-energetic characteristic of the stable Fe-55 radiation source, combined with the infra-red radiation measurement and the beta-radiation measurement, which is essential to the overall success of the invention. For the mono-energetic quantum radiation of the Fe-55 source, the absorption law is strictly exponential with well-defined absorption coefficients which are tabulated and published. From the strictly exponential absorption law, it follows, that all the radiation extinction contributions of the various substances in the investigated web add up mathematically to a resulting extinction signal. In the case of a paper web, these are mainly the components cellulose, fillers and water. Because of the mono-chromatic energy of the Fe-55 radiation source, the extinction caused by each substance can be subtracted from the total extinction measured. Although a selective measurement cannot, therefore, be carried out with the characteristic x-ray radiation alone, in the case of the selective measurement of fillers according to the present invention, the use of the measurement signal obtained by means of the characteristic x-radiation, is of crucial importance in achieving the object according to the present invention in combination with the measurement signals obtained by means of the beta-radiation and the infra-red radiation in order to correct the distorted measurement signals obtained by means of the infra-red radiation.

According to another aspect of the present invention the non-contacting selective measurement of fillers in moving paper webs makes use of the fact that both the filler kaolin and one of the main alternatives to kaolin as a filler, viz. talcum, have distinct but separate absorption bands in the infra-red radiation range. It is therefore possible to obtain an infra-red radiation measurement signal for the first filler component consisting of kaolin and/or talcum, which measurement signal, although requiring correction, is, however, independent of the measurement signal for the second filler component. If, for example, the second filler component is the filler calcium carbonate which cannot be measured by means of infra-red radiation, it is nonetheless possible, with the help of the measurement technique according to the invention, to accurately determine the relative amounts of these filler components. Although the measurement signal obtained by means of the characteristic x-radiation does represent the total extinction caused by kaolin and/or talcum and calcium carbonate as well as cellulose and water, it is, however, possible to accurately determine the x-ray extinction contribution of the substances kaolin and/or talcum, cellulose and water due to the mono-chromatic and stable energy of the characteristic x-radiation used. The absorption coefficients of kaolin and/or talcum, calcium carbonate, cellulose and water for the characteristic x-radiation energy are well-known and defined. With regard to the exponential absorption of the characteristic x-rays which pass through the paper web, the difference between the total extinction measured by means of the characteristic x-radiation and the sum of the extinctions determined for cellulose, kaolin and/or talcum, and water is due solely to the absorption effect of the second filler component calcium carbonate. Therefore one can easily obtain the basis weights of both the filler components. Thus, it is also possible to indicate the relative amount or distribution between both the filler components kaolin and calcium carbonate as well as the total filler content.

Of course, the above observations also apply in the case where the filler calcium carbonate is replaced by titanium dioxide, satin-white or barium sulphate, in the case where both the fillers kaolin and talcum are present at the same time, the measurement of the first filler component is carried out by means of infra-red radiation with both a wavelength absorbed by kaolin and a wavelength absorbed by talcum.

The measurement method according to the invention satisfies a pressing need in paper production and, by giving the paper manufacturer ongoing information on the distribution of two different filler components, it enables him to control the filler composition in such a way that the quality target is achieved using the most economic filler available at any given time. The solution shown is easy to put into practice and is distinguished by the particular advantage that a calibration of the x-ray source based on the type of paper to be measured is not necessary.

Of course the method and system according to the present invention can be used to advantage not only for the selective measurement of fillers in moving paper webs but also generally in all films of thin webs where, of two different filler components, one of the components has a distinct absorption spectrum in the infra-red radiation range and where the total extinction measured by means of mono-energetic characteristic x-rays can be clearly separated or divided into the two filler components and, if applicable, into further substances, provided that these further substances, like the one filler component, also have a distinct absorption band in the infra-red radiation energy. Thin synthetic webs or synthetic foils come to mind here.

The foregoing and other objects and advantages of the invention will appear from the following description. In the description reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
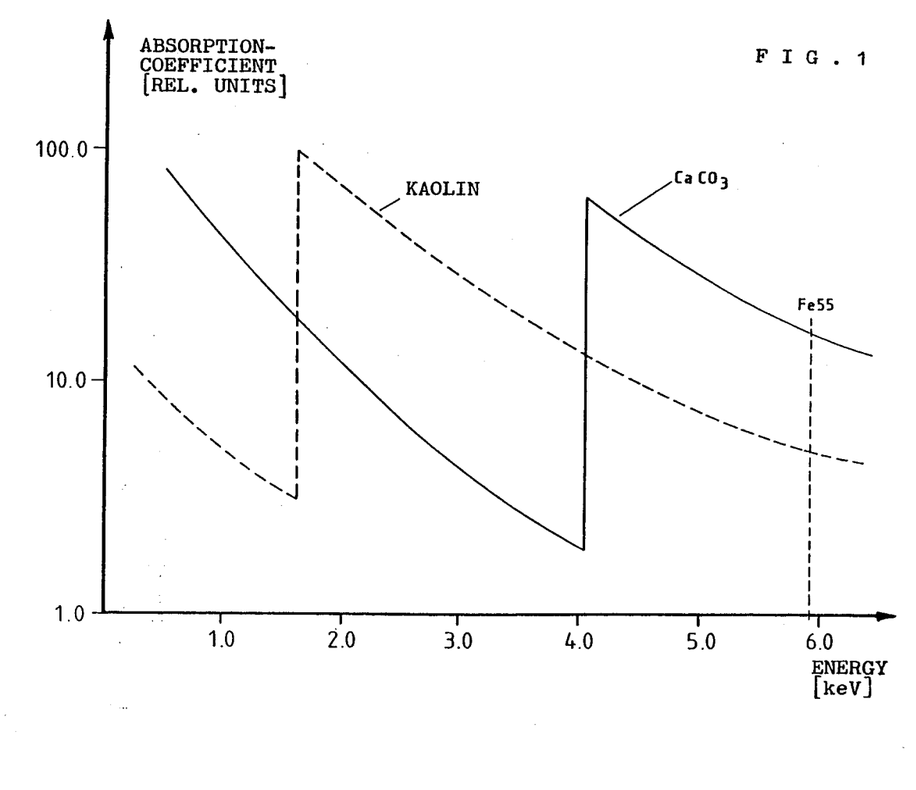
FIG. 1 is a diagram which illustrates for two fillers the absorption coefficient as a function of the radiation energy in the range of several keV.

FIG. 1 shows the typical curves of the absorption coefficients of fillers contained in paper webs, such as kaolin (clay) and calcium carbonate, which contain metal compounds. The absorption edges depicted are characteristic of the metal atoms of the fillers in question. In the diagram of FIG. 1, the position of the quantum radiation of the natural radioactive radiation source Fe-55, which is preferably used for the objects according to the invention, is shown in comparison to the position of the specific absorption edges of kaolin and calcium carbonate.

Figure 2:
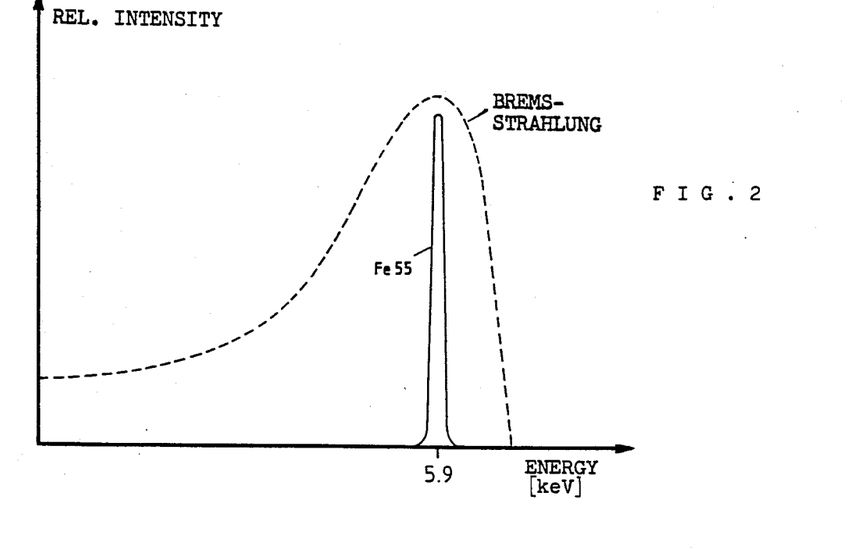
FIG. 2 is a diagram to illustrate the relative intensity of continuous x-radiation and the mono-energetic, characteristic x-radiation of a Fe-55 radiation source as a function of the radition energy.

FIG. 2 illustrates the mono-chromatic energy spectrum of the Fe-55 radiation source (5.9 keV), compared to a continuous x-radiation (bremsstrahlung) which is adjusted to the mono-chromatic radiation energy of the Fe-55 radiation source by choosing the appropriate high voltage.

Figure 3:
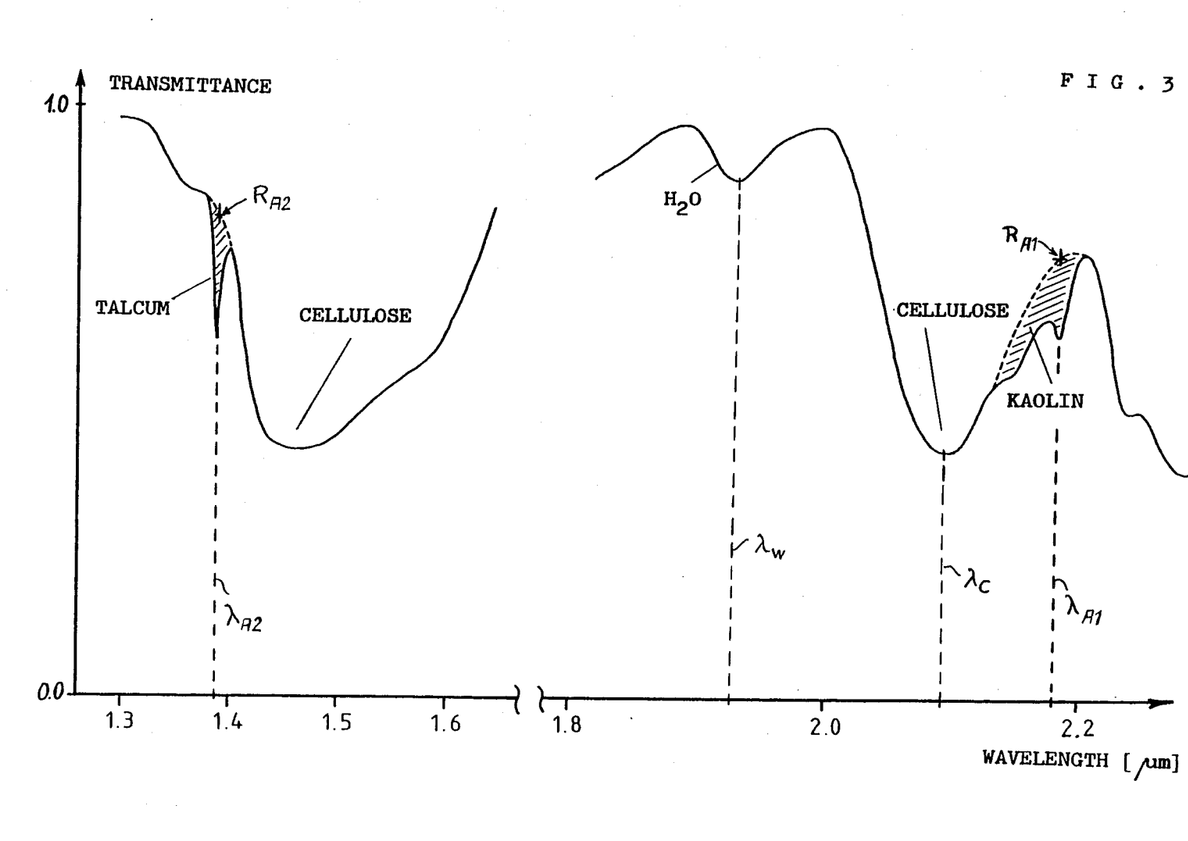
FIG. 3 shows portions of near-infrared spectra showing the absorption of the various components of paper at different wavelengths.

FIG. 3 shows the absorption of the various components of paper in the near-infrared region of the electromagnetic spectrum. Apart from the base material cellulose, the paper web contains the fillers kaolin and talcum, and water. As can be seen, not only cellulose and water but also kaolin and talcum have distinct absorption spectra in the infra-red radiation range which are shown as hatched areas.

If extinction measurements are to be carried out on this paper web, one chooses a measurement wavelength from experience for each of the substances in the paper web the extinctions of which are to be measured, which measurement wavelength is absorbed by the substance in question. Hence a possible wavelength $\lambda_C$ for cellulose, $\lambda_W$ for water, $\lambda_{A1}$ for kaolin and $\lambda_{A2}$ for talcum is shown in FIG. 3. In the case of kaolin and talcum, the zero points $R_{A1}$ and $R_{A2}$ appropriate to each of these substances are also required. In order to give a clear general picture, it was decided to dispense with showing the zero points for cellulose and water as well as two reference wavelengths which could be located at 1.3 and 1.8 $\mu$m respectively. From the state of the art according to German Pat. No. 2,910,673, it is known how the zero points for the measurement wavelengths are obtained from the measurements of intensity of the two reference wavelengths.

Figure 4:
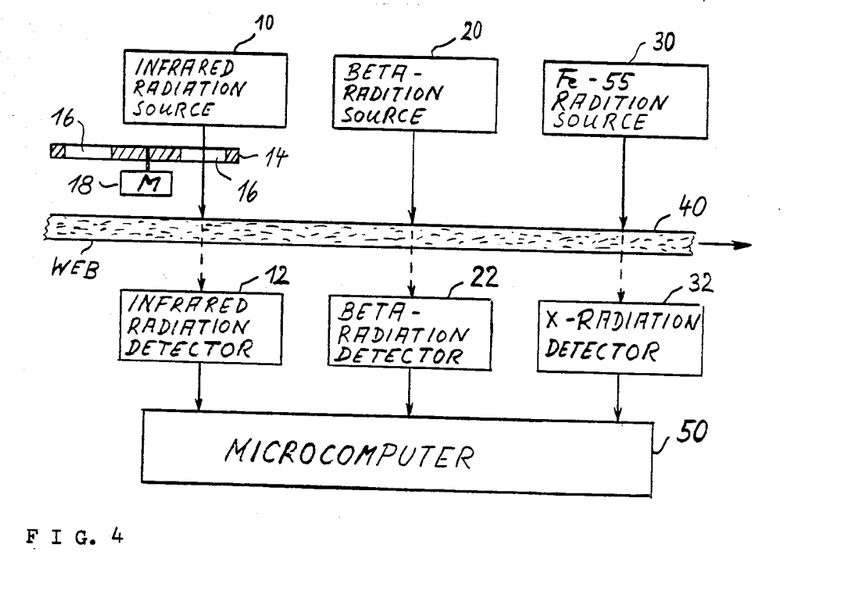
FIG. 4 is a schematic diagram of a measurement system for the implementation of the method according to the invention.

The measurement system of FIG. 4 contains infra-red radiation equipment with an infra-red radiation source 10, a filter wheel 14 driven by a motor 18 and an infra-red radiation detector 12. The beta-radiation measuring equipment contains a beta-radiation source 20 and a beta-radiation detector 22. The mono-energetic x-ray measuring equipment contains an Fe-55 radiation source 30 and an x-ray detector 32.

A thin paper web 40, which is to be measured and which moves continuously in the direction of a shown arrow is irradiated by the sources of the individual measuring systems. In this particular example the filter wheel 14 has five filters 16 of which three are intended for three specific measurement wavelengths (one each), and two are intended for the two reference wavelengths (one each). The measurement signals received from the radiation detectors 12, 22 and 32 are passed on to a micro-computer 50 which processes the measurement signals or, more precisely, the proportional signals derived therefrom, in a manner as shown in the signal flow chart of FIG. 5.

Figure 5:
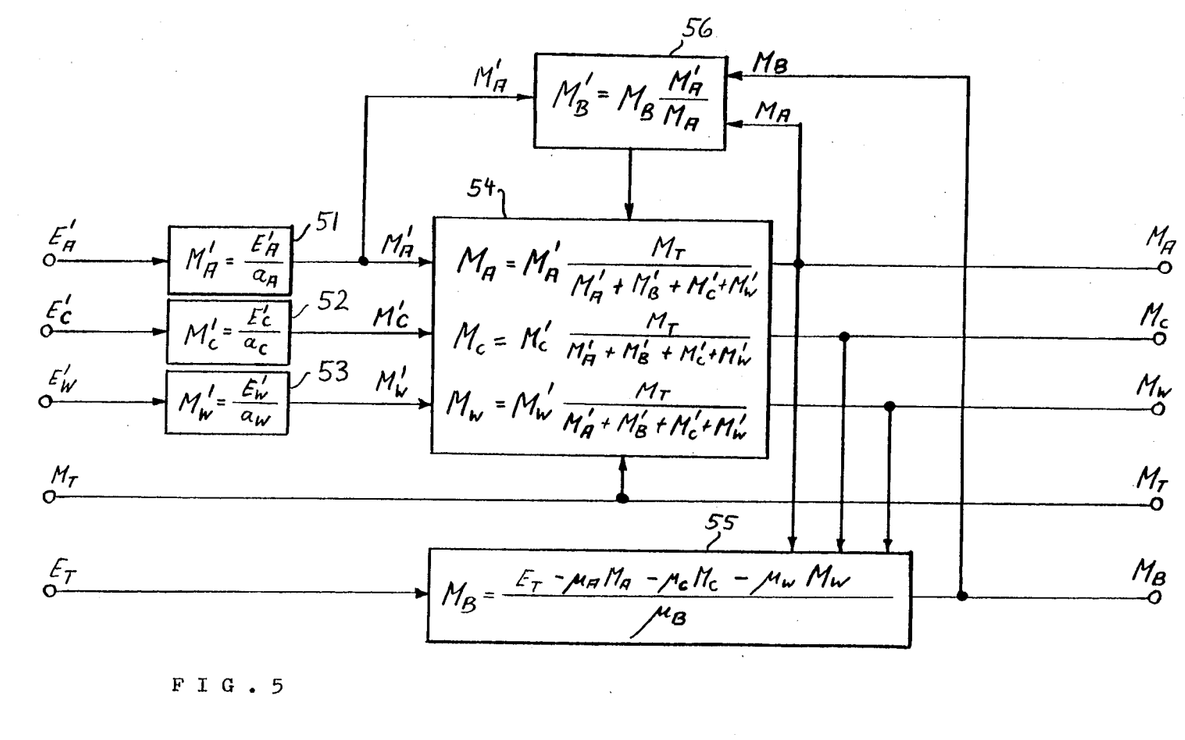
FIG. 5 is a simplified signal flow chart to explain the measurement method according to the invention.

The schematic block diagram of FIG. 4 and the signal flow chart of FIG. 5 shall be considered above all to explain preferred functions according to the invention. Nevertheless, the disclosure herein will suffice a person skilled in the art to implement the invention. The three different measuring systems are well known per se and generally available on the market. The same applies to the micro-computer. A person skilled in the art will have no difficulties to select an appropriate processing means, connect it to the outputs of the measuring systems, and prepare the required program. The micro-computer can be implemented by using, for example, LSI 11 DEC (Digital Equipment Corporation).

For the following observation it is assumed that, in addition to the basic substance cellulose, referred to as C, and the further substance water, referred to as W, the paper web which is to be measured contains a first filler component referred to as A and a second filler component referred to as B. In the example given, the first filler component A is kaolin and the second filler component is calcium carbonate. Hence, a measurement wavelength $\lambda_A$ ($\lambda_{A1}$ in FIG. 3) associated with the kaolin absorption band, is selected by the first of the five filters 16 and similarly $\lambda_C$ and $\lambda_W$ associated with cellulose and water absorption respectively are selected by the second and third filters. The two reference wavelengths $\lambda_1$ and $\lambda_2$ are selected by the two remaining filters.

According to the known equation $$E' = -\ln (I/I_o) \quad (1)$$

an extinction signal $E'_A$ for kaolin, an extinction signal $E'_C$ for cellulose and an extinction signal $E'_W$ for water are obtained from the radiation intensity signals sensed by the infra-red radiation detector 12. In the above equation (1), "I" is the radiation intensity sensed by the detector 12 in the case of one of the measurement wavelengths; "$I_o$" is a zero intensity assigned to the measurement wavelength in question, which is determined from the radiation intensities sensed by the detector 12 at the reference wavelengths $\lambda_1$ and $\lambda_2$, and E' is the extinction measured for the substance related to the measurement wavelength in question.

According to the known equation $$M' = E'/a \tag{2}$$

a measurement signal $M'_A$ for the basis weight of kaolin, a measurement signal $M'_C$ for the basis weight of cellulose and a measurement signal $M_W$ for the basis weight of water is obtained from the extinction signals $E'_A$, $E'_C$ and $E'_W$ measured for the individual substances using the absorption coefficient assigned to each of these substances. In equation (2), "a" is the absorption coefficient of the substance in question for the infra-red measurement wavelength assigned to the respective substance. Accordingly, $a_A$ is the absorption coefficient of kaolin for the measurement wavelength $\lambda_A$, $a_C$ is the absorption coefficient of cellulose for the measurement wavelength $\lambda_C$, and $a_W$ is the absorption coefficient of water for the measurement wavelength $\lambda_W$. These absorption coefficients are known or can also be easily determined experimentally. Due to the absence of an absorption band in the infra-red radiation range in the case of the second filler component calcium carbonate, an infra-red measurement signal for the basis weight of calcium carbonate cannot be obtained.

As described in detail in German Pat. No. 2,910,673, the measurement signals M' obtained by means of infra-red radiation measurement do not correspond to the actual basis weight M of the substances measured in the paper web. Rather it is necessary to multiply the respective measurement signal M' by a correction factor K in order to obtain the respective actual basis weight M.

It has been confirmed in experiments that the following formulation can be made for the correction factor K $$K = \frac{M_T}{M'_A + M'_B + M'_C + M'_W} \tag{3}$$

In equation (3), $M_T$ is the measurement signal for the total basis weight of the paper web obtained by means of beta-rays. The measurement signal $M_T$ is obtained in a known way from the radiation intensity signals provided by the beta-radiation detector 22, while the reference intensity is measured when the paper web is not present. The share or portion in the distortion of the infra-red radiation measurement signals M' caused by the second filler component calcium carbonate is taken into account by a fictitious or theoretical measurement signal $M'_B$ which is unknown for the time being.

To generate the signal $M'_B$ which cannot be measured by means of infra-red radiation, it is assumed that this fictituous or theoretical measurement signal $M'_B$ for the basis weight of the second filler component calcium carbonate contains, if it could be measured by infra-red radiation, a distortion which is proportional to the distortion in the infra-red measurement signal $M'_A$ for the basis weight of the first filler component kaolin. This results in the following equation:

$$\frac{M'_B}{M_B} = \frac{M'_A}{M_A} \tag{4}$$

Here $M_A$ means the true or actual basis weight of the first filler component kaolin and $M_B$ the true or actual basis weight of the second filler component calcium carbonate.

According to the known equation:

$$E_T = -\ln \frac{U}{U_o} \tag{5}$$

one obtains a measurement signal $E_T$ for the total extinction of the paper web from the electrical radiation intensity signals provided by the x-ray detector 32 of the measuring system comprising the Fe-55 radiation source. In equation (5), "U" means the strength of the electrical measurement signal registered by the detector 32 where the paper web is in the measurement gap and "$U_o$" the strength of the electrical signal registered by the detector 32 in the absence of the paper web.

Taking into account the exponential absorption law applying to the characteristic x-ray source used, the following equation can be set up for the measurement signal $E_T$ provided by this measurement system:

$$E_T = \mu_A M_A + \mu_B M_B + \mu_C M_C + \mu_W M_W \tag{6}$$

Here $M_A$ means the basis weight of the filler kaolin present in the paper web, $M_B$ the basis weight of the filler calcium carbonate present in the paper web, $M_C$ is the basis weight of cellulose present in the paper web, $M_W$ the basis weight of the water present in the paper web, $\mu_A$ the absorption coefficient of kaolin for the measurement x-radiation energy of 5.9 keV, $\mu_B$ the absorption coefficient of calcium carbonate for the measurement x-radiation energy of 5.9 keV, $\mu_C$ the absorption coefficient of cellulose for the measurement x-radiation energy of 5.9 keV and $\mu_W$ the absorption coefficient of water for the measurement x-radiation energy of 5.9 keV. These absorption coefficients are known or can easily be determined experimentally.

Equation (6) can be reformulated as follows:

$$M_B = \frac{E_T - \mu_A M_A - \mu_C M_C - \mu_W M_W}{\mu_B} \tag{7}$$

The correction factor K for correcting the measurement signals $M'_A$, $M'_C$, $M'_W$ obtained by means of infra-red radiation can thus be determined with the calculation blocks 51 to 56 given in the signal flow diagram of FIG. 5 by using the measurement signals $M'_A$, $M'_C$, $M'_W$, $M_T$ and $E_T$ obtained from the outputs of the detectors 12, 22 and 32. As can be seen from FIG. 5, signal $M'_B$, which is unknown at first, is a signal which is fed back to the calculation block 54 and it is determined with the help of the output signal $M_A$ of the calculation block 54 itself and the output signal $M_B$ of the calculation block 55, while, in addition to the measurement signal $E_T$, the output signals $M_A$, $M_W$ and $M_C$ of the calculation block 54 are fed to calculation block 55.

The basis weights $M_A$ and $M_B$ determined for kaolin and calcium carbonate can then be related to the total basis weight of the paper web $M_T$ in a usual manner in order, for example, to indicate the percentage content of the individual filler components or the percentage ash content in the paper web. The following equations, for example, can be used for this purpose:

$$P_A = \frac{100 \cdot M_A}{M_T} \tag{8}$$

-continued $$P_B = \frac{100 \cdot M_B}{M_T} \quad (9)$$

$$P_H = \frac{100(M_A + M_B)}{M_T} \quad (10)$$

In the equations (8) to (10), $P_A$ means the percentage content of the first filler component in the paper web, $P_B$ the percentage content of the second filler component in the paper web and $P_H$ the percent ash content in the paper web.

The present invention is not limited to the above embodiment. Various variations and modifications may be made without departing from the scope of the present invention.

I claim:

1. A method for the selective measurement of fillers in a moving web consisting of a stock-mix made up of a base material (C) and two filler components (A, B), and, if applicable, containing a further substance (W), comprising the steps of:
    (a) applying infra-red rays with a measurement wavelength ($\lambda_C$) absorbed by the base material (C), a measurement wavelength ($\lambda_A$) absorbed by the first filler component (A) and, if applicable, a measurement wavelength ($\lambda_W$) absorbed by the further substance (W), as well as at least one reference wavelength ($\lambda_1$) which is not essentially absorbed by these substances (C, A, B, W), and measuring the extinctions ($E'_C$, $E'_A$, $E'_W$) occurring at the web for the individual measurement wavelengths ($\lambda_C$, $\lambda_A$, $\lambda_W$) to obtain a measurement signal ($M'_C$) for the basis weight (grammage) of the base material (C), a measurement signal ($M'_A$) for the basis weight of the first filler component (A) and, if applicable, a measurement signal ($M'_W$) for the basis weight of the further substance (W),
    (b) applying beta-rays to obtain a measurement signal ($M_T$) which represents the entire basis weight (grammage) of the web (T),
    (c) applying a characteristic x-radiation which is absorbed by the base material (C), both the filler components (A, B) and, if applicable, the further substance (W), and measuring the total extinction of the characteristic x-radiation from the web (T) to obtain a measurement signal ($E_T$) which represents the sum of the extinction contributions of the individual substances present in the web, and
    (d) comparing the measurement signal ($M_T$), which represents the entire basis weight of the web, with a signal which is the sum of the measurement signals ($M'_C$, $M'_A$, $M'_W$) for the basis weights of the base material (C), the first filler component (A) and, if applicable, the further substance (W), as well as of a theoretical measurement signal ($M'_B$) for the basis weight of the second filler component (B), to determine a correction factor (K) for correcting the measurement signal ($M'_A$) for the basis weight of the first filler component (A), wherein the theoretical measurement signal ($M'_B$) for the second filler component (B) is obtained by additionally using the measurement signal ($E_T$), which represents the total extinction from the web, and by assuming that the theoretical measurement signal ($M'_B$) for the basis weight of the second filler component (B) has a distortion proportionate to that of the measurement signal ($M'_A$) for the basis weight of the first filler (A).

2. The method of claim 1, comprising the step of using two reference wavelengths ($\lambda_1$, $\lambda_2$), which are not appreciably absorbed by the substances present in the web, to determine a corrected reference value for the radiation intensities measured with the measurement wavelengths of the infra-red rays.

3. The method of claim 1, wherein the radiation intensity is measured for one substance of the web by using an infra-red radiation wavelength specific to this substance, and the measured intensity is corrected in respect of a distortion of intensity which is caused at the measurement wavelength specific to said one substance by a substance which has a different specific measurement wavelength.

4. The method of claim 1, wherein said method is used to take measurements on moving paper webs with cellulose as the base material, with the fillers kaolin and/or talcum as the first filler component, with one of the fillers satin-white, calcium carbonate, titanium oxide and barium sulphate as the second filler component, and with water as the further substance, wherein, in the case where the first filler component consists of the two fillers kaolin and talcum, two measurement wavelengths ($\lambda_{A1}$, $\lambda_{A2}$) in the infra-red radiation range are used for these two fillers (one each), which are absorbed by kaolin and talcum, respectively.

5. The method of claim 2, wherein the radiation intensity is measured for one substance of the web by using an infra-red radiation wavelength specific to this substance, and the measured intensity is corrected in respect of a distortion of intensity which is caused at the measurement wavelength specific to said one substance by a substance which has a different specific measurement wavelength.

6. The method of claim 2, wherein said method is used to take measurements on moving paper webs with cellulose as the base material, with the fillers kaolin and/or talcum as the first filler component, with one of the fillers satin-white, calcium carbonate, titanium oxide and barium sulphate as the second filler component, and with water as the further substance, wherein, in the case where the first filler component consists of the two fillers kaolin and talcum, two measurement wavelengths ($\lambda_{A1}$, $\lambda_{A2}$) in the infra-red radiation range are used for these two fillers (one each), which are absorbed by kaolin and talcum, respectively.

7. The method of claim 3, wherein said method is used to take measurements on moving paper webs with cellulose as the base material, with the fillers kaolin and/or talcum as the first filler component, with one of the fillers satin-white, calcium carbonate, titanium oxide and barium sulphate as the second filler component, and with water as the further substance, wherein, in the case where the first filler component consists of the two fillers kaolin and talcum, two measurement wavelengths ($\lambda_{A1}$, $\lambda_{A2}$) in the infra-red radiation range are used for these two fillers (one each), which are absorbed by kaolin and talcum, respectively.

8. A system for the selective measurement of fillers in a moving web, consisting of a stock-mix made up of a base material (C) and two filler components (A, B), which comprises:
    a multi-wavelength infra-red measuring system for applying infra-red rays to the moving web with a measurement wavelength ($\lambda_C$) absorbed by the base material (C), and a measurement wavelength ($\lambda_A$) absorbed by the first filler component (A), as well as at least one reference wavelength ($\lambda_1$) which is substantially not absorbed by the substances (C, A, B), and measuring the extinctions ($E'_C$, $E'_A$) occurring at the web for the individual measurement wavelengths ($\lambda_C$, $\lambda_A$) to produce a signal ($M'_C$) for the basis weight (grammage) of the base material (C), and a signal ($M'_A$) for the basis weight of the first filler component (A);

a beta-radiation measuring system for applying beta-rays to the moving web to produce signal ($M_T$) which represents the entire basis weight (grammage) of the web (T);

a characteristic X-ray measuring system for applying a characteristic x-radiation to the moving web which is absorbed by the base material (C), and both the filler components (A, B) and measuring the total extinction of the characteristic x-radiation from the web (T) to produce a signal ($E_T$) which represents the sum of the extinction contributions of the individual substances present in the web; and a processor connected to receive the signals ($M'_C$), ($M'_A$), ($M_T$) and ($E_T$) for comparing the signal ($M_T$), which represents the entire basis weight of the web, with a signal which is the sum of the signals ($M'_C$) and ($M'_A$) for the basis weights of the base material (C), and the first filler component (A), as well as of a theoretical signal ($M'_B$) for the basis weight of the second filler component (B), to determine a correction factor (K) for correcting the signal ($M'_A$) for the basis weight of the first filler component (A), and in which the theoretical signal ($M'_B$) for the second filler component (B) is obtained by using the signal ($E_T$), which represents the total extinction from the web, and by assuming that the theoretical signal ($M'_B$) for the basis weight of the second filler component (B) has a distortion which is proportionate to that of the measurement signal ($M'_A$) for the basis weight of the first filler (A).

* * * * *